United States Patent [19]

Aizawa et al.

[11] Patent Number: 5,280,095

[45] Date of Patent: Jan. 18, 1994

[54] FINE PARTICULATE CROSSLINKED TYPE N-VINYLAMIDE RESIN AND MICROGEL, PROCESS FOR PREPARING SAME, AND USE THEREOF

[75] Inventors: Toshiyuki Aizawa; Hitoshi Nakamura, both of Oita; Tetsuhiko Yamaguchi, Kawasaki, all of Japan

[73] Assignee: Showa Denko K.K., Tokyo, Japan

[21] Appl. No.: 723,038

[22] Filed: Jun. 28, 1991

[30] Foreign Application Priority Data

Apr. 23, 1991 [JP] Japan .................. 3-092325

[51] Int. Cl.⁵ .......................................... C08F 20/54
[52] U.S. Cl. .................. 526/307.6; 525/360;
525/366; 525/378; 526/266; 526/271; 526/287;
526/303.1; 526/306; 526/307.1; 526/307.2;
526/307.5; 526/307.7; 526/909
[58] Field of Search ............... 526/307.7, 303.1, 307.6,
526/307.1, 240

[56] References Cited

U.S. PATENT DOCUMENTS

| | | | |
|---|---|---|---|
| 4,623,699 | 11/1986 | Brunnmueller | 525/355 |
| 4,727,116 | 2/1988 | Lange et al. | |
| 4,769,427 | 9/1988 | Nowakowsky | 526/64 |
| 4,873,299 | 10/1989 | Nowakowsky | 526/73 |
| 4,956,400 | 9/1990 | Kozakiewicz | 523/223 |
| 5,008,321 | 4/1991 | Hartmann | 524/378 |
| 5,037,863 | 8/1991 | Kozakiewicz | 523/223 |

FOREIGN PATENT DOCUMENTS

| | | |
|---|---|---|
| 0068159 | 5/1982 | European Pat. Off. |
| 3237308 | 4/1984 | Fed. Rep. of Germany |

Primary Examiner—Bernard Lipman
Assistant Examiner—Fred Zitomer
Attorney, Agent, or Firm—Sughrue, Mion, Zinn, Macpeak & Seas

[57] ABSTRACT

A fine particulate crosslinked type N-vinylcarboxylic acid amide resin having an average particle size of 10 μm or less comprising backbone chains of a homopolymer or copolymer comprising repeating units (A) or (A) and (B) of the formulae:

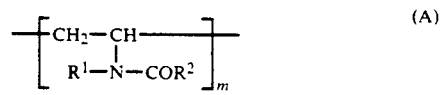

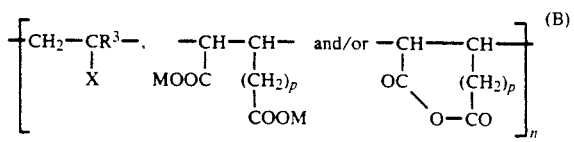

wherein $R^1$, $R^2$ and $R^3$ each independently represent a hydrogen atom or methyl group; X represents a group —COOY, wherein Y represents a hydrogen atom, an alkali metal, a $C_1$-$C_{18}$ alkyl group or a lower alkyl group substituted with hydroxyl group, a dialkylamino group or a quaternary ammonium group; a group —CONHZ, wherein Z represents a hydrogen atom or a lower alkyl group substituted with a dialkylamino group, a quaternary ammonium group, a sulfonic acid or an alkali metal salt thereof; a cyano group, a 2-ketopyrroridinyl group, a lower alkoxy group, a lower acyl group, a lower alkoxycarbonyl group or a lower alkyl group substituted with sulfonic acid or an alkali metal salt thereof; M represents a hydrogen atom, an alkali metal or an ammonium group, with proviso that when $R^3$ is a methyl group, X is not a cyano group, a 2-ketopyrrolidinyl group, a lower alkoxy group, a lower acyl group, a lower alkoxycarbonyl group and a lower alkyl group substituted with sulfonic acid or an alkali metal salt thereof, p represents 0 or 1, and the molar ratio of m:n represents 30-100:70-0.

5 Claims, No Drawings

FINE PARTICULATE CROSSLINKED TYPE N-VINYLAMIDE RESIN AND MICROGEL, PROCESS FOR PREPARING SAME, AND USE THEREOF

BACKGROUND OF THE INVENTION

1. Field of the Invention

The present invention relates to a fine particulate crosslinked type N-vinylcarboxylic acid amide resin, a microgel of the crosslinked type N-vinylcarboxylic acid amide resin comprising said resin swelled (gelled) with water or an organic solvent, and a thickener, dispersion stabilizer or lubricant comprising said microgel as the main component. More specifically, the present invention relates to a fine particulate crosslinked type N-vinylcarboxylic acid amide resin having an excellent chemical stability and affinity for water and organic solvents such as alcohols, particularly exhibiting a high thickening ability, dispersion stability and lubricity by absorbing a liquid in which inorganic or organic ions coexist in the system to be gelled, a microgel having a wide usage in various fields due to the excellent characteristics and functions of said resin, and a hydrophilic (organic solvent-philic) thickener, dispersion stabilizer or lubricant comprising said microgel as the main component.

2. Description of the Related Art

In the prior art, fine particles of a crosslinked hydrophilic gel exist as a dispersion of swelled fine particles in water, and the dispersion thereof is a non-Newtonian flow even at a low concentration, and exhibiting a remarkably high viscosity different from that of a water-soluble linear polymer which exists as a solution in water, as is widely known in the art, and has been variously utilized as a thickener, dispersion stabilizer, lubricant for aqueous gel-like products and cosmetics.

As the crosslinked type fine particles known in the art, for example, synthetic polymers such as the crosslinked type polyacrylic acid (carboxyvinyl polymer) and the crosslinked type acrylic acid copolymer may be included.

These crosslinked type fine particles, however, are all crosslinked products of the polymeric electrolyte type, and therefor, exhibit an excellent thickening ability for water containing no electrolyte but exhibit only remarkably low thickening ability for an aqueous liquid containing a large amount of organic or inorganic ions, such as a natural extract, surfactant, perfume, colorant, reactive dye for printing, and cement slurry. This is considered to be a result of a reduced expansion of the chains because of a suppression of a dissociation of the polymeric electrolyte, which is the backbone chain of the crosslinked product in the presence of ions. Further, when polyvalent metal ions exist, an ion crosslinking occurs through the backbone carboxylic acid, whereby a crosslinked polymer with a substantially higher crosslinking density than required is formed, and this lowers the thickening ability.

To overcome the drawback mentioned above, Japanese Unexamined Patent Publication (Kokai) No. 59-232107 discloses crosslinked type fine particles comprising acrylic acid or methacrylic acid ester copolymerized therein as the crosslinked type acrylic acid copolymer fine particles. This method obtains ion resistant crosslinked type fine particles by introducing nonionic and lipophilic backbone chain constituting units into the polymeric electrolyte backbone chain, but the ratio of (meth)acrylic acid ester copolymerized is as small as 3.5% by weight or less, and the ion resistance is not always satisfactory. Further, if the amount of the hydrophilic monomer is increased, the affinity for water may be lowered, and thus a possibility exists that a transparent gel-like product can not be obtained.

In water absorptive resins known in the art, an aqueous dispersion thereof exhibits a viscosity, but because of greater particle size, the system as a whole becomes nonuniform and therefore, does not exhibit a thixotropic viscous behavior.

Further, among natural polymers, such as those which are not fine particles but exhibit a viscous behavior similar to the crosslinked type fine particles, there may be included natural gums such as gum tragacanth, locust bingham, sodium alginate, carrageenan, and guar gum. These natural polymers, although they contain the groups of electrolytes, exhibit a relatively good thickening ability also for an aqueous liquid containing a large amount of ions. Natural polymers, however, are not only cost-inefficient, but also are susceptible to attack by microorganisms, bringing the problem of corruption, and have a peculiar color and odor, and thus the scope of use thereof is limited.

Crosslinked type fine particles can be obtained according to the preparation processes, in addition to Japanese Unexamined Patent Publication (Kokai) No. 59-232107 described above, disclosed in Japanese Unexamined Patent Publication (Kokai) Nos. 59-80411 and 2-258813, by carrying out a precipitation polymerization in an organic solvent. The crosslinked type fine particles also can be prepared by polymerizing an acrylic acid monomer in an aqueous concentrated solution of a salt. In these publications, however, a preparation example using an N-vinylamide compound is not disclosed.

SUMMARY OF THE INVENTION

Accordingly, an object of the present invention is to eliminate the defects possessed by a thickener by using a water absorptive resin as represented by the sodium polyacrylate crosslinked product, particularly a low thickening ability in a liquid wherein inorganic or organic ions coexist (electrolyte solution) or a low chemical stability which is a drawback of natural polymeric compounds or chemically modified products thereof, and further, develop a substance having an affinity not only for aqueous systems but also for other organic solvents such as alcohols, and also exhibiting a thixotropic and free flowing thickening property instead of a sticky thickening ability (fiber forming property) with a tacky substance.

Other objects and advantages of the present invention will be apparent from the following description.

In accordance with the present invention, there is provided a fine particulate crosslinked type N-vinylcarboxylic acid amide resin having an average particle size of 10 μm or less, comprising the backbone chains of a homopolymer or copolymer comprising the repeating units (A) or (A) and (B) of the formulae:

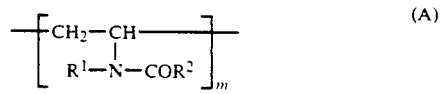

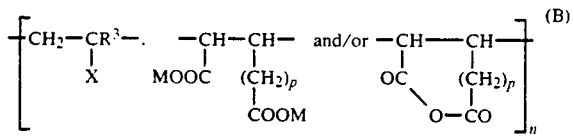

wherein $R^1$, $R^2$ and $R^3$ each independently represents a hydrogen atom or a methyl group; X represents a group -COOY, wherein Y represents a hydrogen atom, an alkali metal, a $C_1$-$C_{18}$ alkyl group or a lower alkyl group, preferably $C_1$-$C_4$ alkyl group, substituted with hydroxyl group, a dialkylamino group or a quaternary ammonium group; a group -CONHZ, wherein Z represents a hydrogen atom or a lower alkyl group substituted with a dialkylamino group, a quaternary ammonium group, sulfonic acid or an alkali metal salt thereof, preferably a $C_1$-$C_4$ alkyl group; a cyano group, a 2-ketopyrroridinyl group, a lower alkoxy group, preferably a $C_1$-$C_2$ alkoxy group, a lower acyl group, preferably a $C_1$-$C_4$ acyl group, a lower alkoxycarbonyl group, preferably a $C_1$-$C_4$ alkoxycarbonyl group or a lower alkyl group, preferably $C_1$-$C_4$ alkyl group substituted with sulfonic acid or an alkali metal salt thereof, M represents a hydrogen atom. an alkali metal (e.g. Na, K) or ammonium group, with a proviso that when $R^3$ is methyl group X is not a cyano group, 2-ketopyrrolidinyl group, a lower alkoxy group, a lower acyl group, a lower alkoxycarbonyl group and a lower alkyl group substituted with sulfonic acid or an alkali metal salt thereof. p represents 0 to 1, and the molar ratio of m:n represents 30 - 100:70 - 0 and a microgel of a crosslinked type N-vinylcarboxylic acid amide resin comprising said resin gelled with water or an organic solvent, and further a thickener, a dispersion stabilizer or lubricant comprising said microgel as the main component.

In accordance with the present invention, there is also provided a process for preparing a fine particulate crosslinked type N-vinylcarboxylic acid amide with an average particle size of 10 μm or less, which comprises precipitation (co)polymerizing 30 to 100 mole % of (A) a compound represented by the formula (I): $CH_2=CHNR^1COR^2$, wherein $R^1$ and $R^2$ each independently represent a hydrogen atom or a methyl group and 0 to 30 mole % of (B) at least one of fumaric acid. maleic acid or itaconic acid or salts thereof, N-vinyl-2-pyrrolidone or compounds of the formula (II):$CH_2=CR^3X$, wherein $R^3$ represents hydrogen atom or a methyl group, X represents a group -COOY, wherein Y represents a hydrogen atom, a $C_1$-$C_{18}$ alkyl group or a lower alkyl group substituted with a hydroxyl group or a dialkylamino group, a group -CONHZ, wherein Z represents a hydrogen atom or a lower alkyl group substituted with a dialkylamino group or sulfonic acid; a cyano group, a lower alkoxy group, a lower acyl group, a lower alkoxycarbonyl group or a lower alkyl group substituted with sulfonic acid, with a proviso that when $R^3$ is a methyl group, X is not a cyano group, a lower alkoxy group, a lower acyl group, a lower alkoxycarbonyl group and a lower alkyl group substituted with sulfonic acid, in a non-aqueous type solvent which dissolves uniformly the reaction components upon initiation of the reaction. and further, converting the carboxyl groups or sulfonic acid groups in the molecules with an alkali metal hydroxide, if necessary.

DESCRIPTION OF THE PREFERRED EMBODIMENTS

Representative specific examples of the respective monomer components of the crosslinked type N-vinylcarboxylic acid amide resin of the above formula are shown above.

Component A: N-vinylformamide, N-vinylacetamide, N-methyl-N-vinylformamide, N-methyl-N-vinylacetamide or the like, particularly preferably N-vinylacetamide.

Component B: acrylic acid, methacrylic acid (hereinafter, called comprehensively (meth)acrylic acid) or their alkali metals salts such as sodium salts and potassium salts; alkyl ester such as methyl, ethyl, propyl, butyl, pentyl, hexyl, heptyl, octyl, nonyl, decyl, stearyl, palmityl or the like;

hydroxy lower alkyl esters such as hydroxyethyl, hydroxypropyl, hydroxbutyl or the like; lower alkyl esters substituted with lower alkylamino groups such as dimethylaminomethyl, dimethylaminoethyl, dimethylaminopropyl, dimethylaminobutyl, diethylaminomethyl, diethylaminoethyl, diethylaminopropyl, diethylaminobutyl or the like; lower alkyl esters substituted with quaternary amino groups such as trimethylammonioethyl ester halides, trimethylammoniopropyl ester halides, triethylammonioethyl ester halides, triethylammoniopropyl ester halides or the like;

amides; amides substituted with lower alkylamino groups such as dimethylaminomethylamide, dimethylaminoethylamide, diethlaminomethylamide, diethylaminoethylamide, diethylaminopropylamide, diethylaminobutylamide or the like; lower alkyl amides substituted with quaternary amino groups such as trimethylammonioethylamide halides, trimethylammoniopropylamide halides, triethylammoethylamide halides, triethylammoniopropylamide halides or the like;

lower alkyl amides substituted with sulfonic acid or alkali metal sulfonic acid such as sulfomethylamide, sulfoethylamide, sulfopropylamide, sulfobutylamide, sodium sulfomethylamide, sodium sulfoethylamide, sodium sulfopropylamide, sodium sulfobutylamide, potassium sulfomethylamide, potassium sulfoethylamide, potassium sulfopropylamide, potassium sulfobutylamide or the like;

acrylonitrile; N-vinyl-2-pyrrolidone; vinyl ethers such as methyl vinyl ether, ethyl vinyl ether, propyl vinyl ether, butyl vinyl ether or the like; vinyl ketones such as methyl vinyl ketone, ethyl vinylketone or the like; lower vinyl carboxylates such as vinyl acetate, vinyl propionate or the like.

Among the above, particularly preferable are (meth)acrylic acid, sodim (meth)acrylate, methyl (meth)acrylate, theyl (meth)acrylate, propyl (meth)acrylate, butyl (meth)acrylate, hydroxyethyl (meth)acrylate, dodecyl (meth)acrylate, and stearyl (meth)acrylate, hydroxypropyl (meth)acrylate, hydroxybutyl (meth)acrylate, dimethylaminoethyl (meth)acrylate, trimethylammonioethyl (meth)acrylate chloride, acrylamide, sulfopropylacrylamide, sulfobutylacrylamide, sodium sulfopropylacrylamide, sodium sulfobutylacrylamide, acrylonitrile. methyl vinyl ether, ethyl vinyl ether, methyl vinyl ketone, ethyl vinyl ketone, vinyl acetate, sodim allysulfonate, N-vinyl-2-pyrrolidone, maleic acid, sodim maleate, itaconic acid, and sodim itaconate.

The copolymer, must contain at least 30 mole % of the component A, as at a ratio lower than that, the ion resistance and absorbability of the organic compounds and the light resistance, which are the specific features of the microgel of the present invention, cannot be fully exhibited. Particularly, when the ion resistance is important, it is preferable to contain 40 mole % or more of the component A, more preferably 50 mole % or more. By incorporating an alkyl ester of acrylic acid or methacrylic acid as the copolymer component, a hydrophobic moiety can formed in addition to the hydrophilic moiety based on the component A in the molecule, thereby obtaining a function like that of a surfactant and thus contributing to a further stabilization of the dispersed particles. However, when used as the hydrophilic thickening agent, the ratio of an alkyl ester of acrylic acid or methacrylic acid is limited to about 5 mole %, and it should be borne in mind that if it is too high, the hydrophobic property is increased, and thus it is possible that the inherent properties of the microgel of the present invention as the hydrophilic thickener may be impaired.

The thickening performance can be further effectively exhibited by adding 20 mole % to less than 50 mole % of anionic components such as acrylic acid, methacrylic acid of the component B, and further, neutralizing the pH to 6-10, if necessary. With less than 20 mole % of the component B or at a pH outside of the above range, the backbone chains of the copolymer will be expanded to a leser extent, whereby the effect of thickening ability will be insufficient although there may be a salt resistance.

For the crosslinking agent usuable in the present invention, a polymerizable compound having at least two unsaturated groups in one molecule is used, and representative specific examples thereof are shown below:

N,N'-lower alkylene bisacrylamides such as N,N'-methylenebisacrylamide, N,N'-1,2-ethylene-bisacrylamide, or the like; alkylene glycol di(meth)acrylates such as ethylene glycol di(meth)acrylate, propylene glycol di(meth)acrylate, or the like;

polyalkylene glycol di(meth)acrylates such as diethylene glycol di(meth)acrylate, triethylene glycol di(meth)acrylate, polyetylene glycol di(meth)acrylate, dipropylene glycol di(meth)acrylate, polypropylene glycol di(meth)acrylate or the like; polyol tri(meth)acrylates such as trimethylolpropane tri(meth)acrylate, pentaerythritol tri(meth)acrylate, or the like;

divinyl compounds such as divinyl benzene,divinyl ether, or the like.

trimethylolpropanediallyl ether, pentaerythritoltriallyl ether, triallyl phosphate, tetraallyloxyethane, sucrose allyl ester or the like.

N,N'-lower alkylenebis(N-vinylcarboxylic acid amide) such as N,N'-methylenebis(N-vinylacetamide), N,N'-1,3-propylenebis(N-vinylacetamide), N,N'-1,4-butylenebis(N-vinylacetamide), N,N'-1,5-pentylenebis(N-vinylacetamide), N,N'1,6-hexylenebis(N-vinylacetamide), N,N'-1,7-heptylene bis(Nvinylacetamide), N,N'-1,8-octylenebis(N -vinylacetamide), N,N'-1,9-nonlylenebis(N-vinylacetamide), N,N'-1,10-decylenebis(N-vinylacetamide), N,N'-diacetyl-N,N'-divinyl-1,3-butanediamine, N,N'-diacetyl-N,N'-divinyl-2,5-hexanediamine, N,N'-diacetyl-N,N'-divinyl-2,4-pentanediamine, N,N'-diacetyl-N,N'-divinyl-2,2-diethyl-1,3-propanediamine, N,N'-diacetyl-N,N'-divinyl-2,5-dimethyl-2,5-hexanediamine, N,N'-diacetyl-N,N'-divinyl-2,4-dimethyl-2,4-pentanediamine, N,N'-diacetyl-N,N'-divinyl-2,2-dimethyl-1,3-propanediamine, N,N'-diacetyl-N,N'-divinyl-2-ethyl-1,5-hexanediamine, N,N'-diacetyl-N,N'-divinyl-2-ethyl-2-methyl-1,3-propanediamine, N,N'-diacetyl-N,N'-divinyl-2-methyl-1,3-butanediamine, N,N'-diacetyl-N,N'-divinyl-2-methyl-1,5-pentanediamine, N,N'-1,3-propylenebis(N-vinylformamide), N,N'-1,4-butylenebis(N-vinylformamide), N,N'-1,5-pentylenebis(N-vinylformamide), N,N'-1,6-hexylenebis(N-vinylformamide), N,N'-1,7-heptylenebis(N-vinylformamide), N,N'-1,8-octylenebis(N-vinylformamide), N,N'-1,9-nonylene-bis(N-vinylformamide), N,N'-1,10-decylenebis(N-vinylformamide), N,N'-diformyl-N,N'-divinyl-1,3-butanediamine, N,N'-diformyl-N,N'-divinyl-2,5-hexanediamine, N,N'-diformyl-N,N'-divinyl-2,4-pentanediamine, N,N'-diformyl-N,N'-divinyl-2,2-diethyl-1,3-propanediamine, N,N'-diformyl-N,N'-divinyl-2,5-dimethyl-2,5-hexanediamine, N,N'-diformyl-N,N-divinyl-2,4-dimethyl-2,4-pentanediamine, N,N'-diformyl-N,N'-divinyl-2,2-dimethyl-1,3-propanediamine, N,N'-diformyl-N,N'-divinyl-2-ethyl-1,3-hexanediamine, N,N'-diformyl-N,N'-divinyl-2-ethyl-2-methyl-1,3-propanediamine, N,N'-diformyl-N,N'-divinyl-2-methyl-1,3-butanediamine, N,N'-diformyl-N,N'-divinyl-2-methyl-1,5-pentanediamine, N,N'-diformyl-N,N,-divinyl-2-methyl-1,5-pentanediamine, N,N'-diacetyl-N,N'-divinyl- 1,3-bis(aminomethyl)cyclohexane, N,N'-diacetyl-N,N'-divinyl-1,4-bis-(aminomethyl)cyclohexane, N,N'-diformyl-N,N'-divinyl-1,3-bis(aminomethyl)cyclohexane, N,N'-diformyl-N,N'-divinyl-1,4-bis(aminomethyl)cyclohexane or the like;

N,N'-diacetyl-N,N'-divinyl-α,ω-diaminopolyesthers) such as N,N'-3-oxa-1,5-pentylenebis(N-vinylacetamide), N,N'-3,6-dioxa-1,8-octylenebis(N-vinylacetamide), N,N'-3,6,9-trioxa-1,11-undecylenebis(N-vinylacetamide), N,N'-3,6,9,12-tetraoxa-1,14-tetradecylenebis(N-vinylacetamide), N,N'-3-oxa-1,5-pentylenebis(N-vinylformamide), N,N'-3,6-dioxa-1,8-octylenebis(N-vinylformamide), N,N'-3,6,9-trioxa-1,11-undecylenebis(N-vinylformamide), N,N'-3,6,9,12-tetraoxa-1,14-tetradecylenebis(N-vinylformamide), N,N'-(1,4-dimethyl)-3-oxa-1,5-pentylenebis(N-vinylacetamide), N,N'-(1,4,7-trimethyl)-3,6-dioxa-1,8-octylenebis(N-vinylacetamide), N,N'-(1,4,7,10-tetramethyl)-3,6,9-trioxa-1,11-undecylenebis(N-vinylacetamide), N,N'-(1,4,7,10,13-pentamethyl)-3,6,9,12-tetraoxa-1,14-tetradecylenebis(N-vinylacetamide), N,N'-(1,4-dimethyl)-3-oxa-1,5-pentylene bis(N-vinylformamide), N,N'-(1,4,7-trimethyl)-3,6-dioxa-1,8-octylenebis(N-vinylformamide), N,N'-(1,4,7,10-tetramethyl)-3,6,9-trioxa-1,11-undecylenebis(N-vinylformamide), N,N'-(1,4,7,10,13-pentamethyl)-3,6,9,12-tetraoxa-1,14-tetradecylenebis(N-vinylformamide) or the like;

N,N'-xylylenebis(N-vinylcarboxylic acid amide) such as p-xylylenebis(N-vinylformylamide), p-xylylenebis(N-vinylacetamide), m-xylylenebis(N-vinylformylamide), m-xylylenebis(N-vinylacetamide) or the like.

Among the above, particularly preferable are N,N'-methylene bisacrylamide, N,N'-1,4-butylenebis(N-vinylacetamide), N,N'-1,6-hexylenebis(N-vinylacetamide), N,N'-1,10-decylenebis(N-vinylacetamide), N,N'-3-oxa-1,5-pentylenebis(N-vinylacetamide), N,N'-3,6-dioxa-1,5-octylenebis(N-vinylacetamide), N,N'-p-xylylenebis(N-vinylacetamide), N,N'-diacetyl-N,N'-divinyl-1,4bis(aminomethyl)cyclohexane, trimethylolpropane tri(meth)acrylate, pentaerythritol tri(meth)acrylate, divinylbenzene, tetraallyl-oxyethane, triallyl phosphate, trimethylolpropane diallyl ether, pentaerythritol triallyl ether, sucrose allyl ether, or the like.

The amount of the crosslinking agent to be used in the present invention is not particularly limited, but is generally 0.01 to 10 mole %, preferably 0.1 to 6.0 mole %, more preferably 0.5 to 4.0 mole %, based on the monomer components. In this connection, if the amount of the crosslinking agent is more than 10 mole % based on the monomer components, the crosslinking density of the resin obtained becomes too high, whereby the swelling ratio will be remarkably lowered to sometimes exhibit no thickening effect. On the other hand, if it is less than 0.01 mole %, the ratio of the polymer chains not crosslinked will be increased, whereby the resin becomes readily soluble in water or an organic solvent to exhibit a fiber forming property, and thus does not have a thixotropic property as the thickener. The mixture of two or more compounds mentioned above can also be used.

The amount of the crosslinking agent is considerably larger than that of the crosslinked hydrophilic resins in general, and this is absolutely necessary for obtaining the desired crosslinking density. However, in the microgels of the present invention, since they are fine particles, no gelatin-like mass is formed and a good flow characteristic can be exhibited in spite of the high crosslinking density thereof.

As the polymerization process for the fine particulate crosslinked N-vinylamide resin according to the present invention, the precipitation polymerization process can be employed.

The process comprises dispersing or dissolving the monomer components and the crosslinking agent in a nonaqueous solvent, thoroughly removing the dissolved oxygen and elevating the temperature to a reaction initiation temperature. Then, an initiator is added to carry out the reaction, and the resin formed with the progress of the reaction is precipitated as fine particles in the solvent. By filtration, drying and maceration of the resin, a fine particulate resin is obtained. As the reaction solvent, there may be employed one which is not necessarily required to uniformly dissolve the reaction components at room temperature, but uniformly dissolves the reaction components (monomer components and crosslinking agent) upon initiation of the reaction, and further in which the resin formed is insoluble, but a stable non-aqueous solvent generally stable during a radical polymerization may be employed without particular limitation. Representative specific examples thereof are set forth below.

Aromatic or aliphatic hydrocarbons such as benzene, toluene, xylene, ethylbenzene, hexane, heptane, octane or the like, aliphatic ketones such as acetone, methyl ethyl ketone, methyl isobutyl ketone or the like, esters such as ethyl acetate, butyl acetate, isopropyl acetate or the like, alkyl amides such as dimethylformamide, dimethylacetamide or the like, sulfoxides such as dimethylsulfoxide or the like, and so on.

Among the above, it is particularly preferable to use benzene, toluene, acetone, methyl ethyl ketone, ethyl acetate, isopropyl acetate.

As the polymerization initiator, peroxides, organic peracids, azobis type compounds which can be uniformly dissolved in the solvent may be employed, and their representative examples are as shown below.

t-butyl peroxide, t-amyl peroxide, cumyl peroxide, acetyl peroxide, propionyl peroxide, benzoyl peroxide, benzoyl isobutyryl peroxide, lauroyl peroxide, t-butyl hydroperoxide, cyclohexyl hydroperoxide, tetralin hydroperoxide, t-butyl peracetate, t-butyl perbenzoate, bis(2-ethylhexylperoxy dicarbonate), 2,2-azobis-i-butyronitrile, phenylazotriphenyl-methane.

Among the above, particularly the use of benzoyl peroxide, t-butyl hydroperoxide, 2,2-azobis-i-butyronitrile is preferred.

The amount of the polymerization initiator to be used in the present invention is not particularly limited, but may be, for example, 0.01 to 5 mole % based on the monomer components, preferably 0.05 to 3 mole %, particularly 0.1 to 2%. In this connection, if the amount of the polymerization initiator is more than 10 mole % based on the monomer components, the polymerization degree of the backbone chain cannot be made higher, but the ratio of the polymer chains not crosslinked will be increased, whereby the polymer tends to become readily soluble in water or an organic solvent and sometimes does not act as a thickener. On the other hand, if the amount of the polymerization initiator employed is less than 0.01 mole %, the conversion of the polymerization reaction cannot be made higher, and thus a drawback arises in that the residual amount of the monomer is increased. Other reaction conditions also are not particularly limited, but may be as generally described below.

Amount of solvent employed: equal to 20-fold of the monomers, preferably equal to 15-fold, particularly equal to 10-fold of the monomers;

Polymerization initiation temperature: 50° C. to the boiling point of the solvent;

Reaction time: about 3 to 8 hours.

The resin thus obtained has a molecular structure in which a linear polymer comprising a homopolymer of an N-vinylcarboxylic acid amide or a copolymer together with other copolymerization components forms the backbone chain, which is crosslinked with a crosslinking agent to give a three-dimensional structure, and primarily, the size of the molecule and the state of the crosslinked state, i.e., the molecular weight, the crosslinking density and the particle size of the backbone chain are most important for obtaining the functions as the thickener, dispersion stabilizer, and lubricant of the resin according to the present invention.

For example, theoretically the thickening performance can be improved by making the backbone chain as large as possible, but the number of molecules not participating in the crosslinking will be increased and the solubility will become higher, whereby the distance between the crosslinks will be increased to remarkably lower the thixotropic property of the gel formed by absorption of the liquid. Therefore, the average polymerization degree of the backbone chain is preferably 500,000 to 100, more preferably 400,000 to 1000, particularly 200,000 to 10,000, and the crosslinking density is 1/10,000 to 1/10, preferably 1/1000 to 3/50, more preferably 1/200 to 1/25.

When the backbone chain is a copolymer, there is slight difference in structure depending on the difference in reactivity of the copolymerized component. For example, when acrylamide, maleic acid, etc. are employed as the copolymerized component, alternate copolymerization will frequently occur, although this depends on the molar ratio charged in the reaction. On the other hand, when acrylic acid, etc. is employed, a block copolymerization will frequently occur, while a random copolymerization well occur in the case of vinyl acetate, etc. However, the difference in structure of the backbone chain copolymer depending to the reactivity of the copolymerized component may add respective characteristic functions in individual use examples, but it is not essential as a whole in the functions as the thickener, dispersion stabilizer, lubricant of the resin according to the present invention.

Further, the fine particulate resins according to the present invention can effect an excellent thickening effect to water, various organic solvents and mixtures thereof, although conventional crosslinked polyacrylic acids, which are typical thickening agents, dispersion stabilizers and bubricants can effect their functions only to water or a mixture of water and a lower alcohol. Typical examples of organic solvents, which can be thickened by the present fine particulate are those mentioned below, which are generally called solvents having a relatively high polarity:

Alcohols such as methanol, ethanol, 1-propanol, 2-buternol, isobutyl alcohol, isoamyl alcohol, cyclopentanol, allyl alcohol, 1,1,1,3,3,3-hexafluoro-2-propanol, 2-methoxyethanol, 2-ethoxyethanol, 2-butoxyethanol, 2-aminoethanol, ethylene glycol, trimethylene glycol, propylene glycol, 1,4-butane diol, 1,3-butane diol, $\alpha,3$-butane diol, triethylene glycol, glycerol; phenols such as phenol, cresol; other solvents such as formaldehyde, acetic acid, 2-pyrrolidinone, dimethyl sulfoxide, pyridine. Furthermore, examples of solvent mixtures of organic solvents, each of which is not thickenable alone or is difficult to be thikened by the present thickner, but which are thickenable as a mixture, are water-organic solvent mixtures such as those of water with, for example, N,N-dimethylformamide, phenol, acetone, tetrahydrofuran, or dioxane; those of organic solvents such as ethanol-acetone, ethanol-chloroform, ethanol-benzene, ethanol-ethylacetate, methanol-methylene chloride, and ethyl acetate-acetic acid.

Although it is not clear why the present resins can thicken the above-mentioned wide variety of solvents, the polarity of the solvent system to be thickned is considered as a measure of the intensity of the interaction between the crosslinked type N-vinyl carboxylic acid amide resin, according to the present absorbent, and the solvent system. As measures for representing the intensity of the polarity of solvents, a dielectric constant ($\epsilon$), a solubility parameter ($\delta$), a solvent polarity parameter ($E_T$ or Z value) and the like are known in the art. As a result of various analyses, the above-mentioned absorbable organic solvents all have an $E_T$ value of 45 or more in the case of a single solvent and an $E_T$ value of 43 or more in the case of a mixed solvent. Further, it has been confirmed that solvents having an $E_T$ value of less than the above-mentioned values are not substantially thicknd by the present adsorbents. Thus, it can be defined that organic solvents which are thicknable by the present resins are those having an $E_T$ value of 45 or more in the case of a single solvent and an $E_T$ value of 43 or more in the case of a mixed solvent. Especially, the good correlations between the $E_T$ value and the thickening effect exist in those having an $E_T$ value of 50 or more, more preferably 53 or more, as either a single solvent or a mixed solvent.

EXAMPLES

The present invention is described in more detail with reference to Examples, which in no way limit the scope of the present invention.

EXAMPLE 1

A solution of 99 g of N-vinylacetamide and 1.0 g of N,N'-methylenebis(acrylamide) as the crosslinkig agent dissolved in 900 g of benzene was boiled, 0.1 g of azobis(isobutyronitirile) was added as the initiator thereto and the boiling state was maintained. With the progress the polymerization, the polymer formed was precipitated into benzene, which was filtered and vacuum dried at 40° C. for 24 hours and macerated, to obtain a white fine powder with an average particle size of 2 $\mu$m.

The thickening ability of the fine powder was evaluated, in terms of a viscosity of 1% dispersion in pure water when neutral (pH 6–8), and the results are shown in Table 1. Further, the salt resistant when sodium chloride was added to the solution was evaluated in terms of the dispersion viscosity. The results are shown in Table 2.

EXAMPLE 2

The reaction was carried out by the same procedure as in Example 1, except that N-vinylformamide was used in place of N-vinylacetamide, to obtain a white fine powder with an average particle size of 4 $\mu$m.

EXAMPLE 3

The reaction was carried out by the same procedure as in Example 1, except that ethyl acetate was used as the polymerization solvent in place of benzene, to obtain a white fine powder with an average particle size of 2 $\mu$m.

EXAMPLE 4

A solution of 70 g of N-vinylacetamine, 30 g of acrylic acid, and 2.0 g of divinylbenzene as the crosslinking agent dissolved in 900 g of ethyl acetate was boiled, 0.4 g of azobisisobutyronitrile was added as the initiator, and the boiling state was maintained. With the progress of the polymerization, the polymer formed was precipitated into ethyl acetate. Then, the same procedure as in Example 1 was carried out to obtain a white fine powder with an average particle size of 2 $\mu$m. The tests of the thickening ability and salt resistance performance were conduct in the same manner as in Example 1, and the results are shown in Table 1 and able 2.

EXAMPLE 5

The reaction was carried out in the same way as in Example 4 except that 55 g of N-vinylacetamide and 45 g of acrylic acid was used in place of 70 g of N-vinylacetamide and 30 g of acrylic acid, to obtain a white powder with an average particle size of 2.5 $\mu$m. The tests of thickening ability and salt resistance were conducted in the same manner as in Example 4, and the results are shown in Table 1 and Table 2.

EXAMPLE 6

A solution of 90 g of N-vinylacetamide, 10 g of methacrylic acid and 1.5 g of tetraallytloxyethane as the crosslinking agent dissolved in 500 g of ethyl acetate was boiled, 0.3 g of benzoyl peroxide was added as the initiator, and the boiling state was maintained. With the progress of polymerization the formed polymer was precidpitatedinto ethyl acetate, and then the same procedure as in Example 1 was carried out to obtain a white fine powder with an average particle size of 2 $\mu$m.

EXAMPLE 7

A solution of 70 g of N-vinylacetamide, 29 g of acrylic acid, 2.0 g of tetraallyloxy-ethane as the crosslinking agent dissolved in 600 g of ethyl acetate was boiled, 0.3 g of benzoyl peroxide was added as the initiator, and the boiling state was maintained. With the progress of the polymerization, the formed polymer was precipitated into ethyl acetate, and then the same procedure as in Example 1 was carried out to obtain a white fine powder with an average particle size of 2 μm.

EXAMPLE 8

A solution of 90 g of N-vinylacetamide, 9 g of methacrylic acid, 1 g of stearyl methacrylate and 1.0 g of pentaerythritol triacrylate as the crosslinking agent dissolved in 900 g of acetone was boiled, 0.3 g of cumyl peroxide was added as the initiator, and the boiling state was maintained. With the progress of the polymerization, the formed polymer was precipitated into ethyl acetate, and then the same procedure as in Example 1 was carried out to obtain a white fine powder with an average particle size of 1.5 μm.

EXAMPLE 9

A solution of 80 g of N--vinylacetamide, 20 g of 2-acrylaide-2-methylpropanesulfonic acid and 0.8 g of N.N'-butylenebis(N-vinyl;acetamide) as the crosslinking agent dissolved in 900 g of acetone was boiled, 0.3 g of cumyl peroxide was added as the initiator, and the boiling state was maintained. With the progress of the polymerization, the polymer formed was precipitated into ethyl acetate. and then the same procedure as in Example 1 was carried out to obtain a white fine powder.

EXAMPLE 10

A solution of 90 g of N-vinylacetamide, 10 g of methyl vinyl ether and 3.0 g of divinyl ether as the crosslinking agent dissolved in 900 g of acetone was boiled, 1.0 g of t-butyl hydroperoxide was added as the initiator, and the boiling state was maintained. With the progress of the polymerization, the formed polymer was precipitated into ethyl acetate, and then the same procedure as in Example 1 was carried out to obtain a white fine powder with an average particle size of 3 μm.

EXAMPLE 11

A solution of 60 g of N-vinylacetamide, 40 g of acrylamide and 3.0 g of N,N'-methylenebisacrylamide as the crosslinking agent dissolved in 900 g of acetone was boiled, 0.4 g of azobisisobutyronitrile was added as the initiator, and the boiling state was maintained. With the progress of the polymerization, the formed polymer was precipitatyed into ethyl acetate, and then the same procedure as in Example 1 was carried out to obtain a white fine powder with an average particle size of 3 μm.

EXAMPLE 12

The reaction was carried out according to entirely the same procedure as in Example 11 except that ethyl vinyl ether was used in place of acrylamide to obtain a white fine powder with an average particle size of 3 μm.

EXAMPLE 13

A solution of 85 g of N-vinylacetamide, 15 g of vinyl acetate and 3.0 g of N,N'-butylenebis(N-vinylacetamide) as the crosslinking agent dissolved in 900 g of acetone was boiled, 0.3 g of azobisisobutyronitrile was added as the initiator, and the boiling state was maintained. With the progress of the polymerization, the formed polymer was precipitated into ethyl acetate, and then the same procedure as in Example 1 was carried out to obtain a white fine powder with an average particle size of 3 μm.

EXAMPLE 14

A solution of 70 g of N-vinylacetamide, 30 g of acrylic acid and 2.5 g of trimethylolpropane trimethacrylate as the crosslinking agent dissolved in 700 g of benzoyl peroxide was boiled, 0.3 g of azobisisobutyronitrile was added as the initiator, and the boiling state was maintained. With the progress of the polymerization, the formed polymer was precipitatyed into ethyl acetate, and then the same procedure as in Example 1 was carried out to obtain a white fine powder with an average particle size of 2 μm.

EXAMPLE 15

The reaction was carried out by the same procedure as in Example 4, except that 40 g of N-vinylacetamide, 30 g of 2-acrylamide-2-methylpropanesulfonic acid and 30 g of acrylic acid to obtain a white fine powder with an average article size of 4 μm.

EXAMPLE 16

The reaction was carried out by the same procedure as in Example 14 except that triallyl phosphate was used in place of trimethylolpropane trimethacrylate to obtain a white fine powder with an average particle size of 4 μm.

EXAMPLE 17

The reaction was carried out by the same procedure as in Example 4, except that trimethylolpropane diallyl ether was used in place of divinylbenzene to obtain a white fine powder with an average particle size of 2 μm.

EXAMPLE 18

The reaction was carried out by the same procedure as in Example 4, except that N,N'hexylenebis(N-vinylacetamide) was used in place of divinylbenzene to obtain a white fine powder with an average particle size of 2 μm.

EXAMPLE 19

The reaction was carried out by the same procedure as in Example 1 except N,N'-(diacetyl)-N,N'-(divinyl)-1,3-bis(aminomethyl)cyclohexane was used in place of N,N'-methylenebis acrylamide to obtain a white fine powder with an average article size of 1 μm.

EXAMPLE 20

The reaction was carried out by the same procedure as in Example 4, except that N,N'-butylenebis(N-vinylacetamide) was used in place of divinylbenzene to obtain a white fine powder with an average article size of 1 μm.

EXAMPLE 21

The reaction was carried out by the same procedure as in Example 4 except methyl ethyl ketone was used in place of ethyl acetate as the solvent to obtain a white fine powder with an average article size of 5 μm.

EXAMPLE 22

The reaction was carried out by the same procedure as in Example 4 except that toluene was used in place of ethyl acetate as the solvent to obtain a white fine powder with an average article size of 1 μm.

EXAMPLE 23

The reaction was carried out by the same procedure as in Example 1 except that isopropyl acetate was used in place of benzene as the solvent to obtain a white fine powder with an average article size of 1 μm.

EXAMPLE 24

Into a solution of 70 g of N-vinylacetamide, 30 g of acrylic acid, 1.5 g of N,N'-butylenebis(N-vinylacetamide) as the crosslinking agent dissolved in 900 g of ethyl acetate was bubbled nitrogen at 1 (liter/min.) for 30 minutes, and the solution then elevated to a temperature of 70° C. As the initiator, 0.3 g of azobisisobutyronitrile was added, and this state was maintained at 80° C. in a nitrogen atmosphere. With the progress of the polymerization, the formed polymer was precipitated into ethyl acetate, and then the same procedure as in Example 1 was carried out to obtain a white fine powder with an average particle size of 1 μm. The tests of the thickening ability and salt resistance were conducted in the same manner as in Example 1, and the results are shown in Table 1 and Table 2.

EXAMPLE 25

The reaction was carried out by the same procedure as in Example 24 except that 100 g of N-vinyl acetamide was used in place of ethyl acetate as the solvent, to obtain a white fine powder with an average article size of 1 μm.

EXAMPLE 26

The reaction was carried out by the same procedure as in Example 25 except that the polymerization temperature was changed from 70° C. to 90° C. to obtain a white fine powder with an average article size of 2.1 μm.

EXAMPLE 27

Into a solution of 70 g of N-vinylacetamide, 29 g of acrylic acid, 1 g of stearyl methacrylate, 2.0 g of pentaerythritol triacrylate as the crosslinking agent dissolved in 900 g of acetone was bubbled nitrogen at 1 (liter/min.)liter/min.) for 30 minutes, and the solution then elevated to a temperature of 50° C. As the initiator, 0.3 g of azobisisobutyronitrile was added, and this state was maintained at 50° C. in a nitrogen atmosphere. With the progress of the polymerization, the formed polymer was precipitated into ethyl acetate, and then the same procedure as in Example 1 was carried out to obtain a white fine powder with an average particle size of 1 μm. The tests of the thickening ability, salt resistance were conducted in the same manner as in Example 1 was carried out to obtain a white fine powder with an average particle size of 1.5 μm.

EXAMPLE 28

The reaction was carried out by the same procedure as in Example 27 except that 95 g of N-vinyl acetamide, 5 g of vinyl acetate, in place of 70 g of N-vinylacetamide, 29 g of acrylic acid, 1 g of stearyl methacrylate, and 2.0 g of trimethylolpropane diallyl ether were used in place of pentaerythritol triacrylate as the crosslinking agent to obtain a white fine powder with an average particle size of 0.2 μ.

EXAMPLE 29

The reaction was carried out by the same procedure as in Example 26 except that 90 g of N-vinylacetamide and 10 g of maleic anhydride was used in place of 70 g of N-vinylacetamide and 30 g of acrylic acid to obtain a white fine with an average article size of 2.0 μm.

Evaluation Tests

1) Thickening ability.

By measuring the 1% aqueous dispersion viscosity, when neutral (pH 6-8), of the fine powders obtained in Examples 1, 4, 5 and 24, the thickening abilities of these fine powders were evaluated. The results are shown in Table 1.

TABLE 1

|  | Example | | | | Comparative Example | | | | | | | |
| --- | --- | --- | --- | --- | --- | --- | --- | --- | --- | --- | --- | --- |
|  | 1 | 4 | 5 | 24 | 1 | 2 | 3 | 4 | 5 | 6 | 7 | 8 |
| Viscosity of 1% dispersion in deionized water (CPS) | 5000 | 10500 | 12000 | 11000 | 65000 | 6000 | 500 | 4000 | 1000 | 7000 | 55000 | 7000 |
| pH of 1% dispersion in deionized water | 6.2 | 6.3 | 6.2 | 6.5 | 6.4 | 6.5 | 6.3 | 6.4 | 6.3 | 6.5 | 6.5 | 8.0 |

Method of Measuring Viscosity of Pure Water Dispersion

Into a tall 200 ml beaker was charged 198 g of deionized water, and 2 g of the fine powder obtained in Example was dispersed therein so that no mass was formed. The viscosity of the 1% aqueous dispersion thus obtained was measured by using a BL type viscometer under the conditions of a No. 4 rotor, 30 rpm, and 320° C. In the Example wherein the monomers containing carboxylic acids such as acrylic acid, methacrylic acid, etc, and anhydride are copolymerized, the viscosity was measured after neutralizing with 10% aqueous NaOH to a pH of 6.0–8.0.

2) Salt Resistance

The salt resistance when sodium chloride was added to the 1% dispersion used in the deionized water dispersion viscosity measurement as described above was evaluated in terms of the dispersion viscosity. The results are shown in Table 2.

Salt Resistance Test

In the 1% aqueous dispersion prepared according to the the deionized water dispersion viscosity measuring method, NaCl wa added and dissolved to the solid concentrations in the liquid as shown in Table 2, and the viscosities were measured.

TABLE 2

| Amount of NaCl added (%) | Example | | | | Comparative Example | | | | | | | |
|---|---|---|---|---|---|---|---|---|---|---|---|---|
| | 1 | 4 | 5 | 24 | 1 | 2 | 3 | 4 | 5 | 6 | 7 | 8 |
| 0 | 5000 | 10500 | 12000 | 11000 | 65000 | 6000 | 500 | 4000 | 800 | 7000 | 55000 | 7000 |
| 0.1 | 3400 | 7200 | 7500 | 7400 | 1000 | 8000 | 230 | 2800 | 400 | 3500 | 2000 | 4500 |
| 0.2 | 2200 | 5400 | 5900 | 5800 | 30 | 28 | 160 | 1800 | 130 | 2600 | 900 | 3000 |
| 0.5 | 520 | 1700 | 2600 | 2400 | 4 | 4 | 100 | 350 | 30 | 950 | 10 | 650 |
| 1.0 | 150 | 550 | 1050 | 950 | 4 | 4 | 100 | 100 | 20 | 550 | 5 | 190 |
| 2.0 | 50 | 240 | 650 | 500 | 4 | 4 | 100 | 80 | 20 | 150 | 5 | 90 |

3) Solubility in Ethyl Alcohol

A 1% dispersion of the fine particles obtained in each Example was prepared with ethyl alcohol (purity 99%), and the solubilities in ethyl alcohol of the resins were compared. The results are shown in Table 3.

4) Dispersion Stability of Talc

To observe the degree of the effect of the dispersibility of the fine particles obtained in the respective Examples, 1% aqueous dispersions of a pH of 6-8 were prepared, and 10 g of the dispersion and 10 g of talc were mixed, and the precipitation after 24 hours was observed. The results are shown in Table 3.

5) Lubricity

To observe the degree of the effect of lubricity, a 0.1% aqueous dispersion of a pH of 6-8 was prepared and the sample solution coated by an applicator to a thickness of 200 μm on a plate made of defatted metal, and the dynamic coefficient of friction was measured immediately by a plane pressurizing member (9 cm²) using a surface characteristic tester (Heidon). The results are shown in Table 3.

TABLE 3

| | Example | | | | Comparative Example | | |
|---|---|---|---|---|---|---|---|
| | 1 | 4 | 7 | 8 | 1 | 2 | 4 |
| Solubility in ethyl alcohol | Dissolved | Swelled | Swelled | Swelled | Insoluble | Insoluble | Swelled |
| Dispersibility of talc | + | + | + | + | ± | − | − |
| Lubricity | + | + | + | + | + | + | − |

Dispersibility of talc
+ : no precipitation observed, and stable dispersion state maintained
± : slight precipitation observed.
− : mostly precipitated.
Lubricity
+ : friction coefficient: less than 0.01 (high lubricity)
± : friction coefficient: 0.1 to 0.3
− : friction coefficient: more than 0.3 (low lubricity).

6) Dissolution in organic solvent

A 100 mg amount of the fine particulate resin obtained in Example 1 was added to 50 ml of organic solvents and it was visually observed how the resins are dissolved in the solvents, while occasionally stirring, at room temperature. The resins having a good solubility were dissolved for 30 minutes to several hours, to increase the viscosity of the solution. Those having no solubility were remained, even after one week, in the form of near white powder. The solubility was evaluated as follows:

+ + : Dissolved within one day
+ : Dissolved at a slow rate
− : Not dissolved even after one week These results are shown, together with the $E_T$ value of each solvent, in Tables 4 and 5 (single solvent) and Table 6 (mixed solvent). There were no solvents in which the resin was dissolved within one day to several days. The abbreviations in Tables 4 to 6 are as follows:
HFIP: 1,1,1,3,3,3-hexafluoro-2-propanol
THF: Tetrahydrofuran
DMSO: dimethylsulfoxide
NMP: N-methylpyrolidinone
DMF: N,N,-dimethylacetamide
$DMA_c$: N,N-dimethylacetamide

TABLE 4

| Solvent | Solubility | $E_T$ |
|---|---|---|
| HFIP | + + | 65.3 |
| water | + + | 63.1 |
| phenol | + + | 61.4 |
| p-cresol | + + | 60.8 |
| glycerol | + + | 57 |
| formamide | + + | 56.6 |
| glycol | + + | 56.3 |
| methanol | + + | 55.5 |
| trimethyleneglycol | + + | 54.9 |
| propylene glycol | + + | 54.1 |
| 1,4-butandiol | + + | 53.5 |
| triethleneglycol | + + | 53.5 |
| 1,3-butandiol | + + | 52.8 |
| 2-methoxyethanol | + + | 52.3 |
| allyl alcohol | + + | 52.1 |
| N-methylacetamide | + | 52 |
| ethanol | + + | 51.9 |
| 2-aminoethanol | + + | 51.8 |
| 2,3-butandiol | + + | 51.8 |
| acetic acid | + + | 51.2 |
| 2-ethoxyethanol | + + | 51 |
| 1-propanol | + + | 50.7 |
| 1-butanol | + | 50.2 |
| 2-butoxyethanol | + + | 50.2 |
| ethyl acetoacetate | − | 49.4 |
| amyl alcohol | − | 49.1 |

TABLE 5

| Solvent | Solubility | $E_T$ |
|---|---|---|
| isoamyl alcoho | + + | 49 |
| 1-hexanol | + | 48.8 |
| isopropyl alcohol | + | 48.6 |
| isobuthyl alcohol | + + | 48.6 |
| 2-pyrolidinone | + + | 48.3 |
| 1-octanol | − | 48.3 |
| 2-butanol | + + | 47.1 |

TABLE 5-continued

| Solvent | Solubility | $E_T$ |
| --- | --- | --- |
| cyclopentanol | + + | 47 |
| acetonitrile | + | 46 |
| DMSO | − | 45 |
| NMP | − | 44.1 |
| DMF | − | 43.8 |
| DMAc | − | 43.7 |
| acetone | − | 42.2 |
| nitroenzene | − | 42 |
| metylene chloride | − | 41.1 |
| pyridine | − | 40.2 |
| chloroform | − | 39.1 |
| ethylacetate | − | 38.1 |
| THF | − | 37.4 |
| chlorobenzene | − | 36.8 |
| 1,4-dixane | − | 36.3 |
| diethylamine | − | 35.4 |
| benzene | − | 34.5 |
| triethylamine | − | 33.3 |
| cyclohexane | − | 32.1 |

TABLE 6

| Solvent mixture | Composition of solvent | Solubility | $E_T$ |
| --- | --- | --- | --- |
| water-dioxane | 0:100 | − | 36 |
|  | 10:90 | − | 46 |
|  | 30:70 | + + | 51 |
|  | 50:50 | + + | 54 |
|  | 100:0 | + + | 63 |
| ethanol-acetone | 0:100 | − | 42 |
|  | 10:90 | − | 47 |
|  | 50:50 | + + | 51 |
|  | 100:0 | + + | 52 |
| chloroform-ethanol | 0:100 | + + | 52 |
|  | 12:88 | + + | 51 |
|  | 50:50 | + + | 48 |
|  | 60:40 | + + | 47 |
|  | 70:30 | + + | 46 |
|  | 80:20 | + + | 46 |
|  | 90:10 | + + | 44 |
|  | 100:0 | − | 39 |
| methanol-methylene chloride | 0:100 | − | 41 |
|  | 4:96 | − | 46 |
|  | 9:91 | + + | 48 |
|  | 39:61 | + + | 51 |
|  | 100:0 | + + | 56 |
| water-acetone | 0:100 | − | 42 |
|  | 20:80 | − | 48 |
|  | 40:60 | − | 51 |
|  | 50:50 | − | 52 |
|  | 60:40 | + + | 53 |
|  | 100:0 | + + | 63 |
| water-THF | 0:100 | − | 37 |
|  | 40:60 | − | 48 |
|  | 80:20 | + + | 51 |
|  | 100:0 | + + | 63 |

Comparative Example 2

A 1% deionized water dispersion was prepared by using a crosslinked type polyacrylic acid (Carbopol 940: B. F. Goodrich) in place of the polymer in Example 1, and the thickening ability and the salt resistance were measured in the same manner as in Example 1. The results are shown in Table 1 and Table 2. Also, evaluations of the ethyl alcohol solubility, dispersion stability of talc, and lubricity were conducted in the same manner as in Example 1. The results are shown in Table 3.

Comparative Example 2

By using a commercially available sodium polyacrylate type water absorbent resin, a 1% aqueous dispersion was prepared and thickening ability and salt resistance were measured in the same manner as in Example 1. The results are shown in Table 1 and Table 2. Also, evaluations of the ethyl alcohol solubility, dispersion stability of talc, and lubricity were evaluated in the same manner as in Example 1. The results are shown in Table 3.

Comparative Example 3

A solution of 70 g of N-vinylacetamide, 30 g of acrylic acid, 20.0 g divinylbenzene as the crosslinking agent dissolved in in 900 g of ethyl acetate was boiled, 0.4 g of azobisisobutyronitrile was added as the initiator and the boiling state was maintained. With the progress of the polymerization, the formed polymer was precipitated into ethyl acetate, and then the same procedure as in Example 1, a white fine powder was obtained. The tests of the thickening ability and salt resistance were conducted in the same manner as in Example 1, and the results are shown in Table 1 and Table 2.

Comparative Example 4

The reaction was carried out by the same procedure as in Comparative Example 3, to obtain a white fine powder. The 1% dispersion exhibited no thixotropic liquid property. The tests of the thickening ability and salt resistance were conducted in the same manner as in Comparative Example 3, and the results are shown in Table 1 and 2. Also, evaluations of the ethyl alcohol solubility, dispersion stability of talc, and lubricity, were made in the same manner as in Example 1. The results are shown in Table 3.

Comparative Example 5

The reaction was carried out in the same manner as in Comparative Example 3, except that the 20.0 g of divinylbenzene of the crosslinking agent was changed to 2.0 g, and the amount of azobisisobutyronitrile of the initiator added was changed 0.4 g to 11.0 g, to obtain a white fine powder. The tests of thickening ability and salt resistance were conducted in the same manner as in Comparative Example 3, and the results are shown in Table 1 and Table 2.

Comparative Example 6

The reaction was carried out in the same manner as in Comparative Example 3 except that the 20.0 g of divinylbenzene was changed to 2.0 g, and the amount of azobisisobutyronitrile of the initiator added was changed 0.4 g to 0.01 g to obtain a white fine powder. The 1% dispersion exhibited no thixotropic liquid property. The tests of the thickening ability and salt resistance were conducted in the same manner as in Comparative Example 3, and the results are shown in Table 1 and Table 2.

Comparative Example 7

The reaction was carried out in the same manner as in Comparative Example 3, except that 20.0 g of the divinylbenzene of the crosslinking agent was changed to 2.0 g, and 30 g of acrylic acid was changed to 109 g of N-vinylacetamide and 90 g of acrylic acid to obtain a white fine powder. The tests of the thickening ability and salt resistance were conducted in the same manner as in Comparative example 3, and the results are shown in Table 1 and Table 2.

Comparative Example 8

A solution of 70 g of N-vinylacetamide, 30 g of sodium acrylate and 0.3 g of N,N'-butylenebis(N-vinylacetamide) dissolved in 400 g of water was adjusted to a temperature of 40V C. As the initiator, 0.4 g of 2,2'-azobis(2-amizinopropane) dihydrochloride was added, and the state of 40° C. was maintained. With the progress of the polymerization, the viscosity of reaction mixture became increased, until it finally became a gelatin-like transparent solid mass. The mass was macerated, dehydrated to remove the water contained in acetone, vacuum dried at 40° C. for 24 hours, and then crushed to obtain a white powder. The 1% dispersion exhibited no thixotropic liquid property. The tests of the thickening ability and salt resistance were conducted in the same manner as in Comparative Example 1, and the results are shown in Table 1 and Table 2.

Application Example 1: Warp glue

Using an aqueous glue solution having the following composition;

| partially saponified polyvinyl alcohol | 7.0 wt. parts |
| processed starch (corn starch) | 3.0 wt. parts |
| acrylic glue | 0.5 wt. parts |
| polymer of Example 4 | 0.3 wt. parts |
| oil agent | 0.6 wt. parts |
| water | 88.6 wt. parts | the glueing, drying and wind-up were carried out for a warp beam comprising 5000 No. 40 cotton monofilament. The glued warp obtained had good physical properties and fabricability.

| Application Example 2: Moisturizing hand lotion | | |
|---|---|---|
| A | deionized water | 85 wt. parts |
| | glycerine | 5 wt. parts |
| | propylene glycol | 1 wt. parts |
| | methyl p-hydroxybenzoate | 0.2 wt. parts |
| | propyl p-hydroxybenzoate | 0.1 wt. parts |
| B | mineral oil | 5 wt. parts |
| | paraffin wax | 1 wt. parts |
| | glycol stearate | 1 wt. parts |
| | acetylated lanoline alcohol | 0.6 wt. parts |
| | dimethicone | 0.5 wt. parts |
| | polymer obtained in Example 7 | 0.2 wt. parts |
| C | triethanolamine | 0.2 wt. parts |
| | PEG-15-cocamine | 0.2 wt. parts |
| D | fragrance | q.s. wt. parts |

The components A were mixed with stirring at 70° C., the oil components, excluding the polymer of Example 7, were mixed, and then the polymer of Example 7 was added and mixed at 70° C. To the componenets A were added the components B, and the mixture was vigorously agitated for 30 minutes, followed by an addition of the componenets C to neutralize the mixture, and the fragrance was added with stirring and the mixture cooled. Thus, a hand lotion having good dispersibility of the oil components and a stable product viscosity with a lapse of time was obtained.

| Application Example 3: Facial Cleansing cream | | |
|---|---|---|
| A | deionized water | 78 wt. parts |
| | polymer of Example 8 | 0.2 wt. parts |
| | glycerine | 5 wt. parts |
| | PEG-8 | 0.5 wt. parts |
| | methyl p-hydroxybenzoate | 0.1 wt. parts |
| | imidazolidinyl urea | 0.3 wt. parts |
| B | paraffin wax | 0.5 wt. parts |
| | capric acid triglyceride | 2 wt. parts |
| | mineral oil | 13 wt. parts |
| C | triethanolamine | 0.2 wt. parts |
| | PEG-15-cocamine | 0.2 wt. parts |

In deionized water was dispersed the polymer of Example 8, and the remainder of the component A was added, followed by stirring at 70° C. The oil components of B were mixed at 70° C., and the components B were added slowly to the components A, the mixture was vigorously agitated, and then the components C were added to neutralize the mixture, followed by cooling with stirring. Thus, a facial cleansing cream with a good dispersion of the oil components and a smooth feeling was obtained.

| Application Example 4: Sun screen lotion | | |
|---|---|---|
| A | deionized water | 81.2 wt. parts |
| | polymer of Example 8 | 0.2 wt. parts |
| | methyl p-hydroxybenzoate | 0.2 wt. parts |
| | propyl p-hydroxylbenzoate | 0.2 wt. parts |
| B | coconut oil | 5 wt. parts |
| C | triethanolamine | 0.2 wt. parts |
| D | octyldimethyl PABA | 5 wt. parts |
| | benzophenone | 3 wt. parts |
| | octyl salicylate | 5 wt. parts |
| E | fragrance | q.s. wt. parts |

In the purified water was dispersed the polymer of Example 8, and the remainder of the components A was added, followed by stirring well. To the components A were slowly added the components B and the mixture was stirred, then the components C were added to neutralize the mixture and the UV-ray absorbers of the components D were uniformly mixed. The resultant mixture was added to a neutralizing solution, stirred, and the perfume was added. Thus, a sun screen lotion with a good dispersion of the UV-ray absorber was obtained.

Application Example 5: Printing glue

A polymer dispersion was obtained by adding 20 parts by weight of the polymer obtained in Example 11 to 70 parts by weight of mineral spirit (isoparaffin mixture having a boiling point of 207°-254° C.), followed by stirring for 20 minutes. Then, 10 parts by weight of sodium carbonate was mixed, while stirring, with the dispersion, followed by stirring for 20 minutes to prepare a 20% polymer mixture.

Using the following black and red dyes, two types of basic printing glue compositions were prepared.

| | Composition A | Composition B |
|---|---|---|
| cold water | 38.5 wt. parts | 32.3 wt. parts |
| silicone antifoamer | 0.25 wt. parts | 0.25 wt. parts |
| surfactant*1 | 0.25 wt. parts | 0.25 wt. parts |
| reactive red 24*2 | 4.0 wt. parts | — |
| reactive black 8*2 | — | 8.0 wt. parts |
| urea | 10 wt. parts | 10 wt. parts |
| sodium m-nitrobenzene sulfonate | 0.5 wt. parts | 0.5 wt. parts |
| hot water | 37.5 wt. parts | 37.5 wt. parts |
| 20% polymer mixture | 6.0 wt. parts | 7.5 wt. parts |
| $KHCO_3$ | 3.0 wt. parts | 2.5 |
| $Na_2CO_3$ | — | 1.2 wt. parts |

*1 hexaoxyethylene nonylphenyl ether
*2 monochlorotriazine dye (Chiba Geigy)

The silicone antifoamer and surfactant were dissolved in cold water in a container provided with an agitator. To this solution, the dye was added, followed by adding the urea and sodium m-nitrobenzene sulfonate dissolved in hot water. Thereafter, the 20% polymer mixture was added and $KHCO_3$ and/or $Na_2CO_3$ were further formulated to obtain the desired printing glue composition.

Using the printing glue composition prepared above cotton fabrics were screen printed. After printing, the printed fabrics were dried at 100° C. for 5 minutes and then steam heated using a saturated streams at 105° C. for 10 minutes, followed by rinsing with cold water. The fabrics were then stirred at 100° C. for 5 minutes in an aqueous solution of Igepal CO-630, followed by rinsing with cold water and drying at 100° C. for 10 minutes. The reflectance R was measured and the lightness (k/s) was calculated from the following equation.

Lightness(k/s)=(100−R)²/2R

Furthermore, the viscosity of the printing glue composition was determined using BH type viscometer at 20 rpm. The results are shown below.

| Composition | Viscosity of composition (cps) | k/s |
|---|---|---|
| A | 12000 | 381 |
| B | 7800 | 2842 |

By using the polymer according to the present invention, it is observed that the compound exhibits a high glue viscosity and good salt resistance.

Furthermore, no substantial legginess is found and the desired screen print can be effected with a good dying ratio by a flowability suitable for the screen printing.

Application Example 6: Zinc Alkalie Battery

A zinc alkali battery provided with an anode cell containing an arrode agent mainly composed of manganese dioxide, a separator and a zinc cathode was prepared according to a conventional manner.

To 196 g of a 40% aqueous potassium hydroxide solution saturated with zinc oxide, 2 g of the polymer obtained in Example 5 was added and iniformly dispersed therein. Further, 10 g of a powder of mercury-zinc alloy containing 0.02% indium, 0.05% lead and aluminum was dispersed to obtain the zinc cathode.

The zinc cathode using the polymer obtained in the present invention exhibited a good stability, because the viscosity thereof was not changed, and no separation due to dispersion and liquid leakage occurred even when the zinc cathode was stored for a long time. Furthermore, the battery obtained therefrom had electrical discharge characteristics such that a continuous discharge time (i.e., a time in which the battery voltage is lowered to 0.9 V) of 5 hours at 20° C.

Application Example 7: Liquid Cleanser

Liquid cleansers having the following formulations were prepared.

|  | Formulation A | Formulation B |
|---|---|---|
| Silicon dioxide (size 2-100 μm) | 7 wt.parts | — |
| Bentonite (size 2-150 μm) | — | 10 wt. part |
| Polymer of Example 14 | 0.3 wt. parts | 0.3 wt. parts |
| Hexaoxyethylene lauryl ether (HLB 12) | 3 wt. parts | 3 wt. parts |
| Ethanol | 3 wt. parts | 3 wt. parts |
| Water | 86.7 wt. parts | 83.7 wt. parts |
| Triethanolamine | q.s. (adjusting to pH 7) | |
| Viscosity of composition(cps) BL type viscosimeter 30 rpm | 1500 | 1800 |

The liquid cleanser using the polymer according to the present invention was maintained in a stable state, without separation, when stored for a long time. Especially, when the system was subjected to a freezing-remelting cycle for a long time, the remelting system exhibited a good stability. Furthermore, since the dispersibility was good, a wide surface area could be cleansed with a small amount of the cleanser and since the viscosity was low, the cleanser was easily shaken out and discharged from the container.

Application Example 8: Liquid Shampoo

Liquid shampoo compositions having the following formulations were prepared.

|  | Composition A | Composition B |
|---|---|---|
| Triethanolamine lauryl sulfate | 20 wt. parts | 18 wt. parts |
| Lauric diethanolamide | 3 wt. parts | — |
| Lauric monoethanolamide | — | 2 wt. parts |
| Propylene glycol | 10 wt. parts | — |
| Polymer of Example 10 | 0.5 wt. parts | — |
| Polymer of Example 10 | — | 0.5 |
| Triethanolamine | 2 wt. parts | 7 wt. parts |
| Bismuth oxychloride (iridescent pigment) | 1 wt. parts | — |
| Zinc pyrithione (water-insoluble bactericide) | — | 1 wt. parts |
| Flavour | q.s. | q.s. |
| Coloring agent | q.s. | q.s. |
| Water | 63.5 | 71.5 |
| Viscosity of composition BL type viscometer 30 rpm | 450 | 500 |

The liquid shampoo using the polymer obtained in the present invention exhibited a good stability, without causing the precipitation of bismuth oxychloride or zinc pyrithine even after storing at 50° C. or room temperature for 3 months. Especially, when the liquid shampoo was subjected to a freezing-remelting cycle for a long time, the remelted shampoo still exhibited a good stability. Furthermore, since the viscosity was low, the shampoo was easily shaken out and discharged from the container.

Application Example 9: Gelled Nail Lacquer Remover

A gelled Nail Lacquer remover having the following formulation was prepared.

| A | Acetone | 288 wt. parts |
|---|---|---|
|  | Deionized water | 38 wt. parts |
|  | Propylene glycol | 38 wt. parts |
|  | Polymer of Example 9 | 8 wt. parts |
| B | PEG-15-cocamine | 8 wt. parts |
| C | Glycerol | 20 wt. parts |

The polymer of Example 9 was dispersed in the acetone, followed by adding the remaining component A and stirring at 70° C. The component B was then gradually added and neutralized and stirred, and finally, the component C was added to obtain a transparent gelled product. The removal effect thereof was good.

Application Example 10: Liquid Detergent (For Soil Adhered to Walls and Ceilings of, For Example, Kitchens)

Liquid detergents having the following formulations were prepared.

|  | Composition A | Composition B |
|---|---|---|
| Sodium dodecylbenzene sulfonate | 3 wt. parts | — |
| Nonaoxyethylene lauryl ether | — | 5 wt. parts |

|  | Composition A | Composition B |
|---|---|---|
| Sodium metasilicate | 2 wt. parts | — |
| Sodium hydroxide | — | 2 wt. parts |
| Polymer of Example 5 | 2.5 wt. parts | 3 wt. parts |
| Water | 92.5 wt. parts | 90 wt. parts |
| Viscosity of composition (cps) BL type viscometer 30 rpm | 4000 | 3500 |

The liquid detergent using the polymer obtained in the present invention exhibited a good stability, without changes in the viscosity or a separation even when the detergent was stored for a long time (at 35° C. for 60 days). Furthermore, the retentionability of the liquid detergent on a vertically placed polypropylene plate was good since, when detergent was attached to the vertical surface of the polypropylene, the detergent did not flow down.

Application Example 11: Liquid Detergent (For Fungus Soil Attached to Tile Joint Portions and Walls of, for Example, Bath Rooms)

Liquid detergents having the following formulations were prepared.

|  | Composition A | Composition B |
|---|---|---|
| Sodium dodecylbenzene sulfonate | 1 wt. part | — |
| Sodium metasilicate | 2 wt. part | — |
| Sodium hydroxide | — | 1 wt. part |
| Sodium hypochlorite | 2 wt. part | 2 wt. part |
| Silicon dioxide | 30 wt. part | — |
| Polymer of Example 14 | 2 wt. part | 3 wt. part |
| Water | 63 wt. part | 94 wt. part |
| Viscosity of composition (cps) BL type viscometer, 30 rpm | 3300 | 7300 |

The liquid detergent using the polymer obtained in the present inventions exhibited a good stability, without changes in the viscosity or a separation even when the detergent was stored for a long time (35° C. for 60 days). Furthermore, the retentionability of the liquid detergent on a vertically placed polypropylene plate was good since, when the detergent was attached to the vertical surface of the polypropylene, the detergent did not flow down.

Application Example 12: Sustained Release Preparation for Oral Cavity (Preparation Comprising an Adhesive Layer and a Medicine Layer Applied by Attaching to Tunica Mucosa Oris)

Oral preparations having the following preparations were prepared.

|  | Preparation A | Preparation B |
|---|---|---|
| (A) Composition for adhesive layer |  |  |
| Polymer of Example 4 | 5 wt. part | 5 wt. part |
| Ethylcellulose | 1 wt. part | 0.2 wt. part |
| Glycerol fatty acid ester | 1 wt. part | — |
| Titanium dioxide | 0.4 wt. part | — |
| Castor oil | — | 0.5 wt. part |
| Ethanol | 60 wt. part | 60 wt. part |
| (B) Composition for medicine layer |  |  |
| Vinyl acetate resin | 10 wt. part | 10 wt. part |
| Hydroxypropylmethyl cellulose | 1 wt. part | 1 wt. part |
| acetate succinate |  |  |
| Triethyl citrate | 0.5 wt. part | 0.5 wt. part |
| Acetone | 10 wt. part | 10 wt. part |
| Methanol | 2 wt. part | 2 wt. part |
| Prostaglandin $E_2$ | 0.1 | — |
| Prostaglandin $E_1$ | — | 0.1 wt. part |

The above composition for adhesive layer was spread over a release paper, followed by drying to obtain an adhesive sheet having a thickness of 100 μm. Then, the composition for the medicine layer was spread over the adhesive layer, followed by drying to form a medicine layer having a thickness of 100 μm.

The sustain-release preparations for an oral cavity according to the present invention can be applied as a sheet-like oral poultice, and a desired long time sustained adhesion and medicine release can be obtained.

Application Example 13: Poultice

A poultice having the following formulation was prepared.

|  | Composition |
|---|---|
| Polymer of Example 4 | 4.5 wt. part |
| Sodium polyacrylate | 2.5 wt. part |
| Glycerol | 20 wt. part |
| Kaolin | 10 wt. part |
| Purified water | 52 wt. part |
| l-Menthol | q.s. |
| Methyl salicylate |  |

The polymer of Example 4 and sodium polyacrylate were dispersed in glycerol, and then a suspension of the kaolin in the purified water was added thereto, followed by adding the methyl salicylate and others. After kneading, the composition was spread over a non-woven fabric to obtain the poultice.

Application Example 14: Gelled Ointment (Transparent)

A 3 g amount of the polymer obtained in Example 5 was swollen in 25 g of distilled water. On the other hand, 3 g of ketoprofene and 2 g of hydroxypropyl cellulose (HPC-M available from Nippon Soda K. K.) were dissolved in a mixed solvent of 39 of ethanol and 10 g of isopropanol and the resultant solution was added to the above-prepared polymer, followed by thoroughly stirring. To the resultant mixture, 0.4 g of diisopropanol amine dissolved in 17.6 g of distilled water was added and stirring was effected until the mixture became totally uniform, to thus obtain the desired translucent gelled ointment composition.

5 Application Example 15: Gelled Ointment (Creamy)

A 2 g amount of the polymer obtained in Example 5 was swollen in 66 g of distilled water. On the other hand, 3 g of ketoprofen and 1 g of polyethleneglycol monostearate (MYS-40 available from Nikko Chemicals K. K.) were dissolved in a mixed solvent of 39 g of ethanol and 10 g isopropanol and the resultant solution was added to the above polymer, followed by thoroughly stirring. To this mixture, 0.4 g of diisopropanol amine dissolved in 17.6 g of distilled water was added, followed by thoroughly stirring until the mixture became totally uniform, to obtain the desired white creamy ointment composition.

The fine particulate crosslinked type N-vinylamide resin of the present invention has an excellent chemical stability, an affinity for water and polar solvents such as alcohols, is little influenced by the effect of metal ions, if any, in the system, exhibits a high thickening ability and dispersing stability by absorbing and gelling these liquids, and yet the thickening action does not produce a tacky substance having a fiber forming property, but extremely fine microgels, and thus provides numerous excellent effects not found in the thickener with water absorptive resins known in the art. More specifically, the fine particulate crosslinked type N-vinylamide resin of the present invention has the ability to exist as a dispersion of fine particles by gelling with various aqueous solutions containing electrolytes or certain kinds of organic solvents, and said gel dispersion has a thixotropic property, whereby functions and effects such as a thickening ability, dispersibility (dispersion stability), and lubricity can be exhibited. Also, where a high strength is not required, such as in aromatic agents for domestic use, a form imparting property can be exhibited by use at a relatively higher concentration, and further, it has an ability to slowly release water, alcohols, and pharmaceutical held therein by absorption. Therefore, the fine particulate crosslinked type N-vinylacetamide resin and the hydrophilic microgel of said resin has a wide diversity of applications that required such characteristic functions.

Specific representative examples of these uses, such as those as set forth below, may be mentioned. Of course, these are merely exemplary, and the use of the resin of the present invention is not limited thereto.

1) Commodity, toiletary, cosmetics, pharmaceutical fields:

Heat mediums (heat accumlant, exothermic, heat insulator), aromatic, deodorant, drying agent, liquid detergent, soft finishing agent, cleanser, toothpaste, shampoo, emulsion stabilizer such as lotion, humectant, lubricant, sustained release pharmaceutical (oral, parenteral, percutaneous agents), external agents (poultice, ointment, trauma coating agent), mucosa administration (protective) preparation, lubricants for the intrabody insertion type medical instruments, materials for dentrifice.

2) Agricultural, horticultural, civil engineering construction fields:

Coating of seed, fertilizer, agricultural medicine preparation improvement (binder, slow release), improvement of soil, medium, prevention of frost, dew formation.

3) Chemicals for industrial use:

Lubricants, glues, electrolytes supports (battery, sensor).

The specific use methods and the amount used of the crosslinked type N-vinylamide resin of the present invention depend on the respective uses, and cannot be generally defined, but as a rule, will be different from the standard embodiments in the respective uses. Nevertheless, a use example not found in the prior art can be expected due to the excellent functions and effects thereof, and the amount can be reduced to the extent of the effect required.

We claim:

1. A fine particle crosslinked N-vinylcarboxylic acid amine resin having an average particle size of 10 μm or less comprising backbone chains of a homopolymer of copolymer comprising repeating units (A) or (A) and (B) of the formulae:

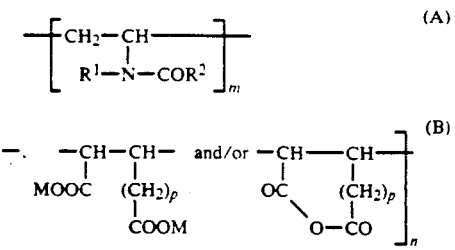

wherein $R^1$, $R^2$ and $R^3$ each independently represents a hydrogen atom or a methyl group, x represents a group -COOY, wherein Y represents a hydrogen atom, an alkali metal atom, a $C_1$-$C_{18}$ alkyl group or a lower alkyl group substituted with a hydroxyl group, a dialkylamino group or a quaternary ammonium group; a group CONHZ, wherein Z represents a hydrogen atom or a lower alkyl group substituted with a dialkylamino group, a quaternary ammonium group, a sulfonic acid group or an alkali metal salt thereof; a cyano group, a 2-ketopyrralidinyl group, a lower alkoxy group, a lower acyl group, a lower alkoxycarbonyl group or a lower alkyl group substituted with a sulfonic acid group or an alkali metal salt thereof; M represents a hydrogen atom, an alkali metal atom, or an ammonium group, with a proviso that when $R^3$ is a methyl group, x is not a cyano group, a 2-ketopyrrolidinyl group, a lower alkoxy group, a lower acyl group, a lower alkoxycarbonyl group and a lower alkyl group substituted with a sulfonic acid group or an alkali metal salt thereof, p represents 0 and 1, and the molar ratio of m:n represents 30-100:70-0, said resin being produced by the steps of:

precipitation (co)polymerizing 30 to 100 mol % of (A) a compound having the formula (I):$CH_2=CHNR^1COR^2$, wherein $R^1$ and $R^2$ are the same as defined above and 0 to 70 mol % of (B) at least one of fumaric acid, maleic acid or itaconic acid or anhydrides thereof, N-vinyl-2-pyrrolidone or compounds having the formula (II):$CH_2=CR^3X$, wherein $R^3$ and X are the same as defined above, in the presence of at least one crosslinking agent select from the group consisting of:

N-N'-1,4-butylenebis(N-vinylacetamide),
N-N'-1,6-hextlenebis(N-vinylacetamide),
N,N'-1,10-decylenebis(N-vinyllacetamide),
N,N'-3,6-dioxa-1,5-pentylenebis(N-vinylacetamide),
N,N'-xylylenebis(N-vinylacetamide), and
N,N'-diacetyl-N,N'-divinyl-1,4-bisaminomethylcyclohexane, in a non-aqueous solvent which uniformly dissolves the reaction components upon initiation of the reaction and converting the carboxyl groups or sulfonic acid groups in the molecules with an alkali metal or ammonium hydroxide, if necessary.

2. A particulate crosslinked N-vinylcarboxylic acid amide resin as claimed in claim 1, wherein the backbone chain has an average polymerization degree of 100 to 500,000 and a crosslinking density of 1/200 to 1/25.

3. A fine particulate crosslinked N-vinylcarboxylic acid amide resin as claimed in claim 1, wherein $R^2$ in the unit (A) is a methyl group.

4. A fine particulate crosslinked N-vinylcarboxylic acid amide resin as claimed in claim 3, wherein $R^1$ in the unit (A) is a hydrogen atom.

5. A fine particulate cross-linked N-vinyl carboxylic acid amide resin as claimed in claim 1, wherein the amount of the crosslinking agent is 0.5 to 4.0 mole %, based on the monomer components.

* * * * *